United States Patent
Thong et al.

[11] Patent Number: 6,035,232
[45] Date of Patent: Mar. 7, 2000

[54] DEVICE FOR DETERMINING TACHYCARDIAC HEART RHYTHM DISTURBANCES

[75] Inventors: Tran Thong, Lake Oswego, Oreg.; Amiran Sh. Revishvili, Moskau, Russian Federation

[73] Assignee: Biotronik Mess-und Therapiegeraete GmbH & Co., Berlin, Germany

[21] Appl. No.: 09/146,192

[22] Filed: Sep. 3, 1998

Related U.S. Application Data

[63] Continuation of application No. 09/073,830, May 6, 1998, abandoned
[60] Provisional application No. 60/045,850, May 7, 1997.

[51] Int. Cl.$^7$ .................................................. A61B 5/0468
[52] U.S. Cl. ........................................................ 600/510
[58] Field of Search .................................. 600/510, 518, 600/515, 519

[56] References Cited

U.S. PATENT DOCUMENTS

| | | |
|---|---|---|
| 4,860,749 | 8/1989 | Lehmann . |
| 5,107,850 | 4/1992 | Olive . |
| 5,243,980 | 9/1993 | Mehra . |
| 5,325,856 | 7/1994 | Nitsche et al. . |
| 5,327,900 | 7/1994 | Mason et al. . |
| 5,379,776 | 1/1995 | Murphy et al. . |
| 5,383,910 | 1/1995 | den Dulk . |

FOREIGN PATENT DOCUMENTS

| | | |
|---|---|---|
| 0 094 758 | 11/1983 | European Pat. Off. . |
| 0 302 577 | 2/1989 | European Pat. Off. . |
| 0 580 128 | 1/1994 | European Pat. Off. . |
| 0 597 459 | 5/1994 | European Pat. Off. . |
| 0 597 459 A2 | 5/1994 | European Pat. Off. . |
| 0 647 150 | 4/1995 | European Pat. Off. . |
| 0748 638 A2 | 12/1996 | European Pat. Off. . |
| 44 39 256 | 5/1995 | Germany . |

OTHER PUBLICATIONS

Jenkins et al, "A Single Atrial Extrastimulus Can Distinguish Sinus Tachycardia from 1:1 Paroxysmal Tachycardia", PACE, vol. 9, Nov.–Dec. 1986, Part II, pp. 1063–1068.

*Primary Examiner*—Scott M. Getzow
*Attorney, Agent, or Firm*—Venable; Robert Kinberg; Michael P. Leary

[57] ABSTRACT

A device for determining tachycardial heart rhythm disturbances, comprising: a stimulation pulse generator; a ventricular stimulation electrode; an electrode line; one sensor electrode each in the atrium and ventricle of a heart; an atrial action detecting device; a ventricular action detecting device; a timer; an atrial interval detecting device; a ventricular interval detecting device; a comparator unit which compares the chronological spacings of successive atrial actions and successive ventricular actions and outputs a stimulation inducing signal; an evaluation device for detecting and evaluating changes, caused by the ventricular stimulation pulse in the atrial intervals and for outputting a tachycardia classification signal that characterizes the outcome of the evaluation; and a stimulation control device connected on the output side to the stimulation pulse generator, for controlling the output of a train of stimulation pulses at such intervals as occur between the stimulation pulses of a plurality of spontaneous ventricular actions at a time, with the definition of an interval varying within the train in a predetermined way, of each ventricular stimulation pulse from the preceding or next expected spontaneous ventricular action.

10 Claims, 7 Drawing Sheets

DEVICE FOR DETERMINING TACHYCARDIAC HEART RHYTHM DISTURBANCES

CROSS-REFERENCE TO RELATED APPLICATION

This application is a continuation of application Ser. No. 09/073,830 filed May 6, 1998 now abandoned, which claims the benefit of U.S. application Ser. No. 60/045,850 filed May 7, 1997, the subject matter of both applications being incorporated herein by reference.

BACKGROUND OF THE INVENTION

The invention relates to a device of the generic type defined by the preamble to claim 1.

Such a device can be embodied as a stand-alone diagnostic device, or as a component of an implantable cardiac pacemaker with an anti-tachycardial mode of operation, a defibrillator, cardioverter, or combination device having the function of both of the above devices.

The therapy of tachycardial disturbances in heart rhythm is one of the most important fields in cardiology and is especially a primary field of application of electrostimulation of the heart.

In view of the many ways these problems can be manifested and their many causes, extensive attempts have been made in recent years to improve the preconditions for therapeutic success by more-precise classification of tachycardial arrhythmias and more-exact association with typical defects in the cardiac stimulus conduction system. Because they are comparatively widespread and need treatment, on the one hand, and on the other because of the good chances of successfully treating them using special pacemaker pulse trains, the problem of reliably distinguishing pathological ventricular tachycardias from other forms of arrhythmia—such as physiological tachycardias, ventricular fibrillation or supra ventricular tachycardias—and under differentiated conditions as well—has come to be recognized as especially important.

European Patent Application EP 0 094 758 A2 has proposed that a criterion for the presence of a pathological tachycardia be obtained by comparing a current time interval between successive heartbeats with a previously determined mean value on the one hand and with a predetermined (fixed) value on the other. Thus some progress was gained compared with the earliest diagnostic methods, which were based solely on the evaluation of the current heart rate and could not distinguish physiological tachyarrhythmias from pathological ones. For exact classification of the various types of tachycardia, however, the confidence level of this method is insufficient.

In a further development of this method, it is proposed in German Patent Disclosure DE 44 39 256 A1 that the relative distribution of heartbeat intervals, which can be considered fibrillation intervals or tachycardia intervals, within predetermined ranges of time be used in order to classify the prevailing type of arrhythmia. This is intended to take into account the fact that the internal lengths often overlap considerably in practice between ventricular tachycardia on the one hand and fibrillation on the other. However, since in the final analysis classification is done solely on the basis of the intervals between ventricular actions (called the "RR intervals"), the problem cannot be attacked at its roots by proceeding in this way.

Later, various proposals have been made—for instance in European Patent Disclosure EP 0 302 577 A2—that the signal form of the EKG (taken conventionally or intracardially) be used as the distinguishing and even predicting criterion. The EKG signal form, however, does not adequately reliably reflect the occurrence of ventricular tachycardia, and the high signal resolution needed to achieve a fair confidence level entails very high expense for measurement and processing, which is hardly feasible in an implantable pacemaker.

In the proposal for tachycardia classification made in European Patent Disclosure EP 0 580 128 A1, the expense is increased still further by the additional provision of an activity sensor and of processing means for the sensor signals.

Quite a number of other approaches—which will not be discussed in detail here—make use of analysis of the spatial propagation or correlation of depolarization in the heart tissue. This requires the implantation of many electrodes for signal detection—and for this reason if no other has very little likelihood of realization.

In U.S. Pat. No. 4,860,749, a method for distinguishing a ventricular tachycardia from a sino- or other kind of supraventricular tachycardia is described, in which the atrial and ventricular heart rate (the respective reciprocals of which are also called the "PP interval" and "RR interval" below) and the AV interval (hereinafter sometimes also called the "PR interval") are measured. If the RR interval is within a predetermined range and is shorter than the PP interval, then the status is readily classified as ventricular tachycardia. If the atrial and ventricular rates are approximately the same as a consequence of 1:1 AV conduction or retrograde conduction, then the measured AV interval is subjected to a comparison with a predetermined value ("sino-AV interval"), and from the result of the comparison the classification criterion is obtained.

Proceeding in this way is also employed in the version proposed in U.S. Pat. No. 5,107,850, but in which further processing follows: For the case where the measured AV interval is longer than the predetermined one, the "regularity" (a measure of the constancy over time) of the measured AV intervals and the ventricular rate (whose reciprocal will hereinafter also be called an RR interval) are ascertained and evaluated, but this requires still a second predetermined value for the AV interval. On the basis of -additional measurement of the atrial rate and the determination of the regularity and of the atrial and ventricular rates, an atrial tachyarrhythmia can be classified.

The procedure is also quite similar in U.S. Pat. No. 5,383,910.

In these last-named methods, the specification of one or even two different AV values, which is typically done the first time the device is programmed, puts additional adaptation parameters into play, which can limit the efficiency of the algorithm employed considerably if they are not aptly chosen at the outset or if they become invalid without being noticed—for instance as a consequence of physiological changes in the patient.

U.S. Pat. No. 5,325,856 proposes a method for distinguishing between ventricular and supraventricular tachycardias, which is based on a comparison of the divergence over time in the PR and RR values, with two predetermined threshold values at the onset of the tachycardia. Once again, largely arbitrarily selected parameters play a decisive role in classifying the arrhythmia statuses, which involves the risk of mistaken associations.

U.S. Pat. No. 5,327,900 describes a method for distinguishing between pathological and physiological tachycardias at comparable atrial and ventricular rates, which is based on associating the measured AV interval with a predetermined AV time slot that has been determined from the AV interval during normal sinus rhythm. This algorithm is comparatively simple; however, so far there is no evidence of adequate efficiency of discrimination on its part.

Another method, in which a great number of additional criteria (on the RR interval and on the ratio between the PP and RR intervals) is employed to ascertain the treatability of an ascertained tachyarrhythmia in the event of virtual agreement between the atrial and ventricular rates, is describes in U.S. Pat. No. 5,379,776.

From J. M. Jenkins et al, "A Single Atrial Extra Stimulus Can Distinguish Sinus Tachycardia from 1:1 Paroxysmal Tachycardia", PACE Vol. 9/II (1986), and J. M. Jenkins and S. Caswell, "Detection Algorithms in Implantable Cardioverter Defibrillators", Proc. IEEE 84, No. 3, 428 (1996), a method is known in which by early atrial stimulation and by observation of the ventricular reaction, a distinction can be made between sinus tachycardia on the one hand and other types of tachycardia on the other, such as ventricular tachycardia with retrograde 1:1 conduction. However, the distinction possible with this method is of little clinical value; for the operation of a cardioverter defibrillator, especially, a distinction between ventricular tachycardia (VT) that requires treatment and supraventricular tachycardia (SVT) that does not require treatment must be made.

In EP 0 597 459 A2, a method based on this is described, in which if the RR and PP intervals match, first a comparison of the length of the AV or PR interval with a predetermined base value is made and finally—if this does not lead to a conclusive result—a test stimulation pulse train with a predetermined elevated pulse rate is emitted and the classification is done on the basis of the stimulated heart response, in particular changes over time in the RR intervals and in the magnitude of the AV interval. This procedure involves the danger of inducing or accelerating a ventricular tachycardia.

In EP 0 647 150 A1, a device for distinguishing between ventricular and supraventricular tachycardias is described, in which in synchronization with the R wave, the fat cushion adhering to the sino-atrial and/or AV node is stimulated, and the tachycardia is classified as a function of the ascertained change in heart rhythm. This requires that additional electrodes be implanted along with a conventional stimulation electrode line and therefore increases the expense and effort of the operation and the risks for the patient.

SUMMARY OF THE INVENTION

The object of the invention is therefore to disclose a simply designed, easily implanted device, that entails minimal risks to the patient, for detecting various tachycardial disturbances in heart rhythm and with which especially a distinction can be made between ventricular and supraventricular tachycardias.

This object is accomplished according to the invention by performing stimulation to induce a heart response, which can be used for unequivocal tachycardia classification, while avoiding additional electrodes and high-rate pulse trains. It also includes the concept of disclosing a device that has means for first, on the basis of the spontaneous heart activity signals, picked up by one probe each in the atrium and in the ventricle, performing an initial classification in which the length of the RR and PP intervals is evaluated both in amount and in their ratio to one another. If a so-called 1:1 tachycardia is found (in which the RR intervals are approximately equal to the PP intervals), then while maximally using the existing means, a more extensive classification is made on the basis of the response of the atrium to a train of ventricular individual stimuli with successive output times that are shifted relative to the time of spontaneous ventricular actions (VES="Ventricular Early Stimulus"). If the atrium actions detected follow along with the time shift of the stimuli relative to the spontaneous ventricular actions, then ventricular tachycardia (VT) with retrograde conduction is involved. Conversely, if the PP intervals remain essentially constant, then a supraventricular tachycardia (SVT) is involved, and if no unambiguous tendency can be made out, this is an indication of the presence of occasional atrial conduction and is again evidence of an SVT.

Between the individual stimuli in the train, a number of spontaneous ventricular actions is weighted out, to assure a recovery of spontaneous cardiac activity.

The device according to the invention is comparatively uncomplicated to produce and implant, and on implantation and in operation puts no greater burden on the patient than a conventional cardiac pacemaker/cardioverter.

BRIEF DESCRIPTION OF THE DRAWINGS

Advantageous further features of the invention are defined by the dependent claims and described in further detail below along with the description of the preferred embodiment of the invention, in conjunction with the drawings. Shown are:

DETAILED DESCRIPTION OF THE INVENTION

Figure 1:
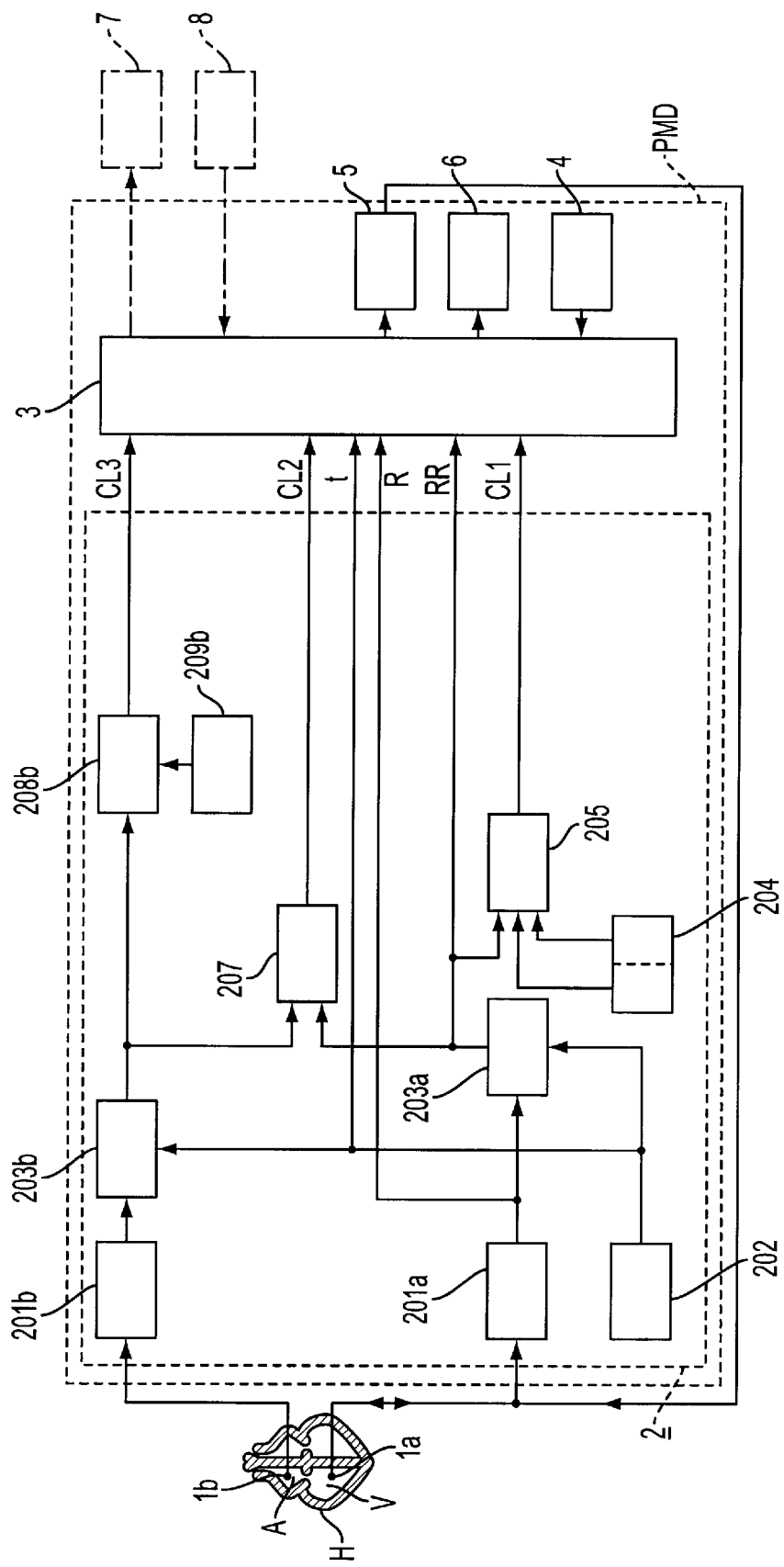
FIG. 1 a function block circuit diagram of a device of one embodiment of the invention.

In FIG. 1, the layout of a device for tachycardia classification, especially for distinguishing between ventricular tachycardia and supraventricular tachycardia, in an embodiment of the invention is shown in terms of its essential function elements, the device being connected to a heart H via a ventricular electrode 1a and an atrial electrode 1d, as endocardial signal pickups. The device includes a detection and evaluation unit 2 and a control unit (controller) 3 and is controlled in accordance with a flow or sequence explained hereinafter that is stored in a program memory. On the basis of classification signals output by the device, a pacemaker pulse generator 5 or defibrillator 6, known per se, is selectively triggered for suitable electrotherapy. The component groups 2–6 (with other components, such as a power supply, that is known per se and therefore not shown here) form a combined pacemaker/defibrillator PMD.

The classification data output by the detection and evaluation unit 2 may be displayed on an optionally provided display unit 7 (symbolically represented by a dashed line) and thus used if necessary independently of the introduction of electrotherapy as well—for instance in order to determine a therapy using medication. Also optionally, an input unit 8 is provided for inputting patient-specific data pertaining to the carrying out of a specific classification procedure.

At least some parts of the detection and evaluation unit 2 and/or controller 3 may be realized for special applications—for instance for attendant use in heart surgery, including in a separate appliance—independently of a cardiac pacemaker and/or cardioverter.

In both cases, the practical embodiment will advantageously be made with a microprocessor structure or partially on an ASIC (customer-specific circuit) basis, and the function elements described below are embodied at least in part by software.

As shown in FIG. 1, the detection and evaluation unit 2 has a sensor amplifier 201*b*, connected to the atrial sensor electrode 1*b*, for sensing electrical activity (of the P waves) in the atrium A of the heart H, and a sensor amplifier 201*a*, connected to the ventricular sensor electrode 1*a*, for sensing electrical activity (especially the R waves or QRS complexes) in the ventricle B of the heart H. A timer or clock generator 202 is also provided, for detecting the moment the respective electrical activity occurs.

A ventricular interval detecting device 203*a* connected on the input side to the ventricular electrode la and to the timer 202—and which in the simplest version is basically an R-wave-triggered counter for the pulses of the timer, but in the preferred embodiment performs averaging of the counted values over a number of R waves—ascertains the (averaged) time intervals between successive electrical activities in the ventricle (RR intervals). Analogously, an atrial interval detecting device (in the simplest version, a P-wave-triggered counter) 203*b*, connected on the input side to the atrial activity detector 201*b* and to the timer 202, serves to ascertain the—optionally averaged—time intervals between successive electrical activities in the atrium (PP intervals). Averaging of the measured time intervals in the first and second computation units 203*a*, 203*b* is done in a manner known per se by means of an integration or averaging device (not shown), for instance on the basis of a number of four detected heart actions.

A two-range threshold value memory 204 is used to store one lower and one upper threshold value for the ventricle intervals, of which the upper one demarcates a range of normal heart activity from a range of tachycardia rhythm disturbances, while the lower threshold value is the upper limit for a range of heart activity to be classified as ventricular fibrillation. A two-stage comparator 205*a* is connected to the outputs of the ventricular interval detecting device 203*a* and the threshold value memory 204, for comparing the ventricular intervals (or mean interval values) with the lower and upper threshold values and for outputting a first classification signal CL1 characterizing the result of the comparison—i.e., the location of the ascertained RR intervals in one of the two ranges mentioned.

A further comparator stage 207, for comparing the atrium time intervals with the ventricle time intervals and for outputting a second classification signal CL2 characterizing the outcome of the comparison, is connected to the output of the atrial interval detecting device 203*b*. The layout of the comparator stage 207 is shown in more detail in FIG. 2 and will be described hereinafter.

Also connected to the output of the atrial interval detecting device 203*b* is an atrial interval evaluation unit 208*b*, which is embodied for outputting a third classification signal CL3 that characterizes the outcome of an evaluation described in further detail hereinafter. Each evaluation operation is tripped via a control signal from the controller 3. A criteria memory 209*b* serves to store a predetermined evaluation criterion.

Along with the classification signals CL1–CL3, the controller 3 directly receives an output signal R, characterizing the detection of a ventricular action, of the ventricular action detecting device 201*a*; the time or clock signal t of the timer 202; and the output signal RR of the ventricular interval detecting device 203*a*. The processing of these signals in the controller 3 and the flow control will also be described hereinafter.

Figure 2:
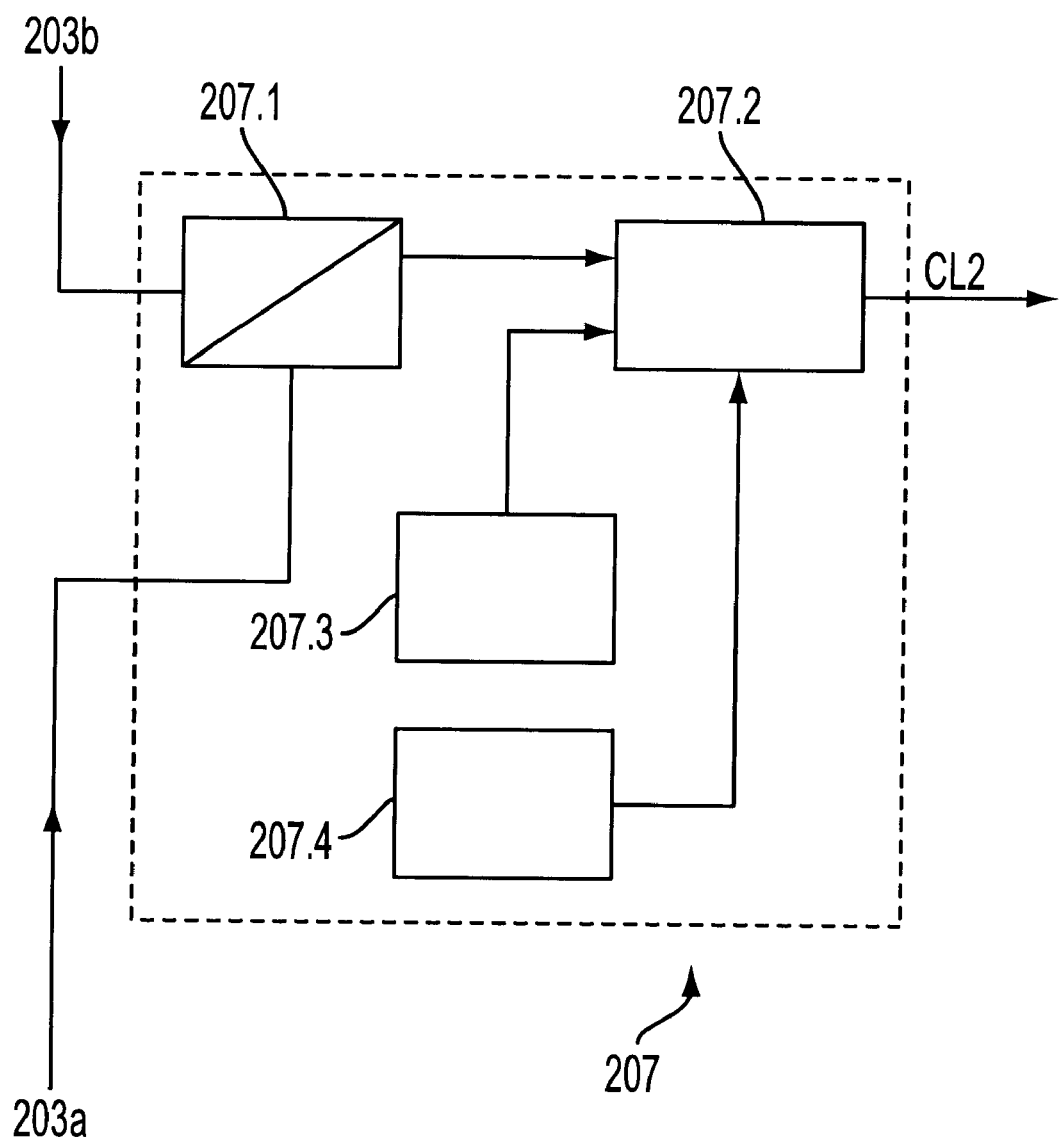
FIG. 2, a schematic illustration of the layout of the comparator unit 207 of the device of FIG. 1.

FIG. 2—again schematically—shows the layout of the comparator stage 207.

Connected to the outputs of the interval detecting devices 203*a* and 203*b* (not shown in this drawing figure) are the two inputs of a divider stage 207.1, which performs a division of the respectively supplied RR interval by the associated PP interval, and whose output is connected to one input of a comparator stage 207.2, to which it furnishes the calculated current value of this quotient. The other comparison signal input of the comparator stage is connected to a quotient memory 207.3, in which fixedly predetermined integral values (in particular, the value 1) for the RR/PP quotient are stored, and which can therefore be embodied as a read only memory (ROM). In a further memory 207.4, preferably embodied as a reprogrammable memory (such as a EEPROM), a quotient tolerance value is stored, which is furnished via a third input to the comparator stage 207.2. Thus—within the limits of the predetermined tolerance range—the second classification signal CL2 output at the output of this comparator stage expresses whether the quotient of the RR interval divided by the PP interval is a whole number and in particular whether its value is approximately 1.

Figure 3:
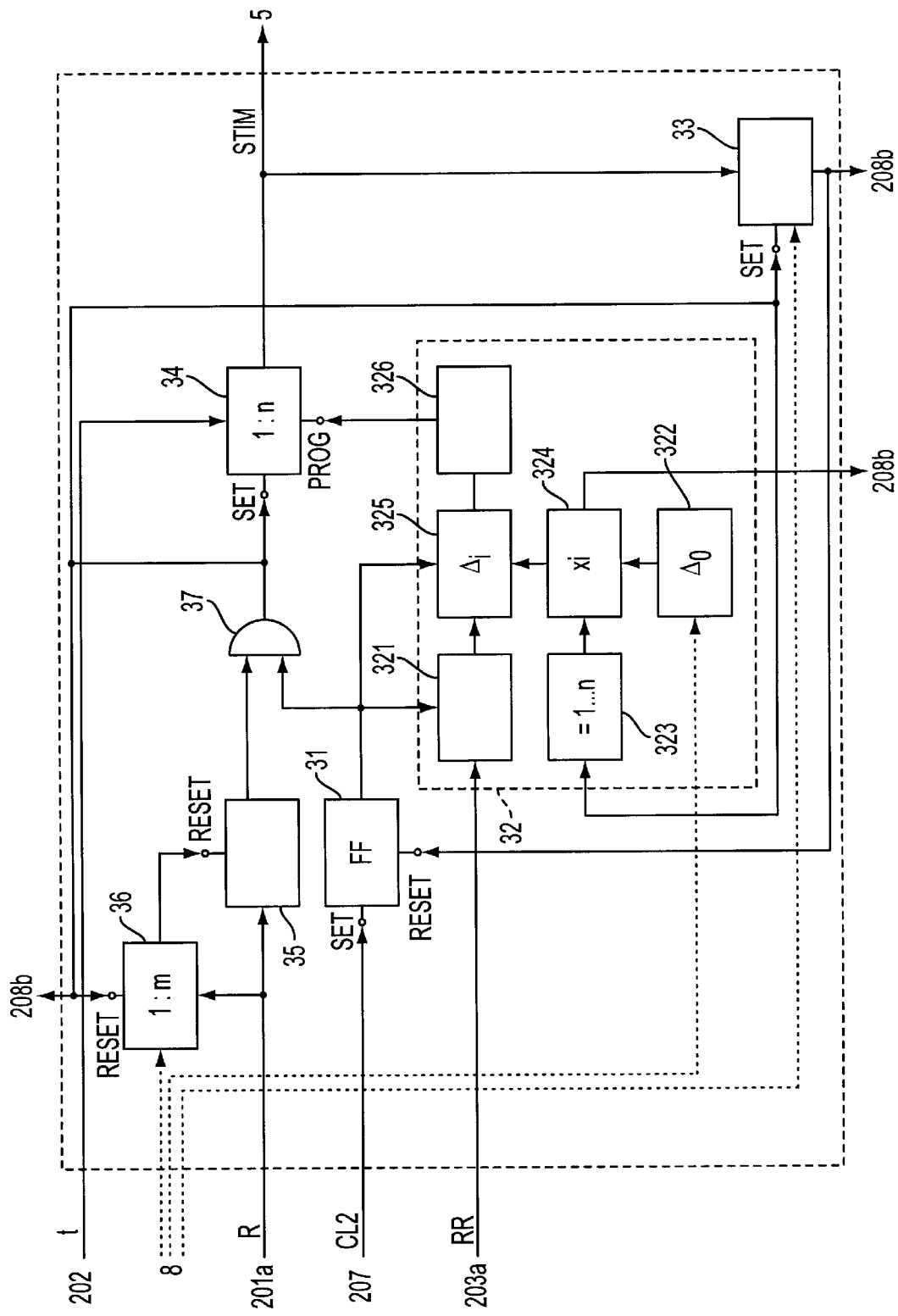
FIG. 3, a detailed illustration of the layout of the stimulation control device 3 of the device of FIG. 1.

In FIG. 3, essential components of the controller 3 are shown in the form of a simplified block circuit diagram for carrying out one embodiment of the invention.

A flip-flop 31, connected via its set input to the output of the comparator stage 207 (FIGS. 1 and 2)is connected on its output side to the control input of a stimulation time calculating unit 32 and via its reset input to the output of a programmable 1:n divider 33. The data input of the stimulation time calculating unit 32 (whose layout will be sketched hereinafter) is connected to the output of the ventricular interval detecting device 203*a*, and its output is connected to the programming input of a programmable counter 34. The data input of this counter is connected to the timer 202 (FIG. 1), whose output in turn is connected to the pacemaker pulse generator 5 and supplies an activation signal thereto when the programmed counting value is attained. Each counting by the counter 34 is initiated via a control input, which is triggered as follows:

The controller 3 also has a blocking member 35, which is connected on the input side to the output of the ventricular action detecting unit 201*a* (FIG. 1), and which is reset by a programmable 1:m divider 36. The output of the blocking member 35 is connected to one input of an AND gate 37, whose other input is carried to the output of the flip-flop 31. The output of the AND gate 37 is connected to control inputs of the dividers 33 and 36, of the counter 34, and of the stimulation time calculating unit 32 and triggered these components.

The calculation device 32 includes a ventricular interval memory 321, connected to the output of the ventricular interval detecting device 203*a*; a programmable base decrementing memory 322; and a counter 323 connected on the input side to the output of the AND gate 37; as well as a multiplier stage 324, connected to the output of the counter and to the decrementing memory; and a subtraction stage 325 connected to the output of the multiplier stage and to the ventricular interval memory 321. The output of the ventricular interval memory is connected both to the atrial interval evaluation unit 208b (FIG. 1) and to a stimulation interval memory 326, whose output forms the output of the calculation unit 32.

Figure 4:
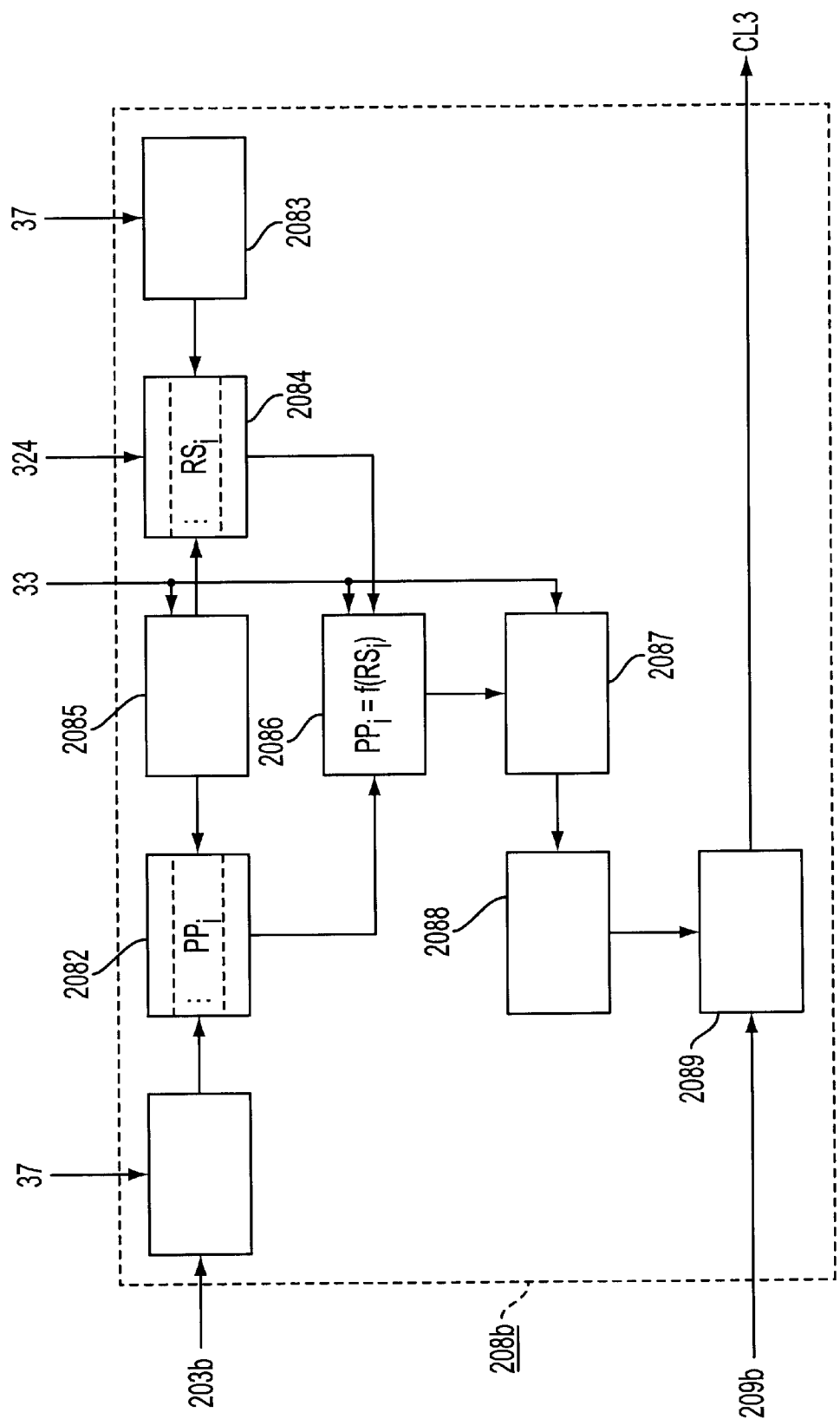
FIG. 4, a detailed illustration of the layout of the atrial internal evaluation unit 208b of FIG. 1.

FIG. 4—again in the form of a schematic function block circuit diameter—shows the layout of the evaluation unit 208b of FIG. 1 in one embodiment. It includes an atrial interval memory 2082, which is connected to the output of the atrial interval detecting device 203b (FIG. 1) via a memory write controller 2081, and a ventricular interval decrementing memory 2084, connected to the output of the multiplier stage 324 (FIG. 3) via a separate memory write controller 2083. The atrial interval memory 2082 and the ventricular interval decrementing memory 2084 are embodied as serial multi-range memories for storing a predetermined number n of differential interval values $PP_i$ of predetermined atrial actions and preceding decrementing values $\Delta_i$ and $RS_i$, corresponding to these actions, of the ventricular action stimulus intervals.

The memory write controllers 2081, 2083 are triggered by the aforementioned AND gate 37. A memory read controller 2085, triggered by the divider 33 (FIG. 3), causes the memory contents to be read out into a correlator stage 2086 if the output state of the divider changes, and in the same way the correlator stage 2086 itself, an approximation unit 2087 following it, and a differentiation memory 2088 following that, are activated. The output of the differentiation memory is connected to one input of a rise comparator 2089, whose other input is connected to the criteria memory 209b (FIG. 1) and whose output forms the classification signal CL3.

The operation of the device described above in terms of its basic layout will now be described by additionally referring to FIGS. 5a and 5b, which together form a flow chart on the procedure for demonstrating a VT or distinguishing it from an SVT. This procedure is especially advantageous in the simultaneous presence of an atrial tachyarrhythmia, which proceeds with the same or a higher rate as the tachyarrhythmia demonstrated and to be classified in the ventricle.

After the start of the procedure, in the first calculation unit 203a the time interval (RR interval) between two successive ventricular actions (R-wave signals), sensed in a manner known per se by the ventricular electrode 1a and processed in the associated detecting device 201a, is determined.

In two successive steps S1 and S2, via the comparator 205, first in a comparison with the interval threshold values stored in the memory 204 an association is made with one of the following interval or rate ranges:

(1) "normal" sinus activity (relatively long interval or low rate values), or
(2) tachyarrhythmia states to be classified further (medium-sized interval or rate values for a tachyarrhythmia state), or
(3) fibrillation range (very short interval values or high rate values). The two threshold values should be programmed patient-specifically and by the physician.

If it is found that the ventricular interval value is not located in either a tachycardial range (2) ("no" in step S1) in the fibrillation range (3) ("no" in step S2), and is thus in the range (1), then the initiation of an electrotherapy can be omitted ("stop" after S2). Conversely, if it is in range (3) ("yes" in step S2), then as a rule, via the controller 3 which has received and processed the corresponding classification signal CL1, the defibrillator 6 is triggered and defibrillation or cardioversion is initiated. If needed, the physician can also administer medication, once the presence of ventricular fibrillation has been shown to him on the display 7 as an outcome of the classification.

If the current RR interval or ventricular rate value is in the range (2) or (3) ("yes" in step S1), then in a step S3 (which is optional and therefore shown in dashed lines) it can additionally be asked whether the tachyarrhythmia was of sudden onset. (The components required for this are not shown in FIG. 1.)

Figure 5A:
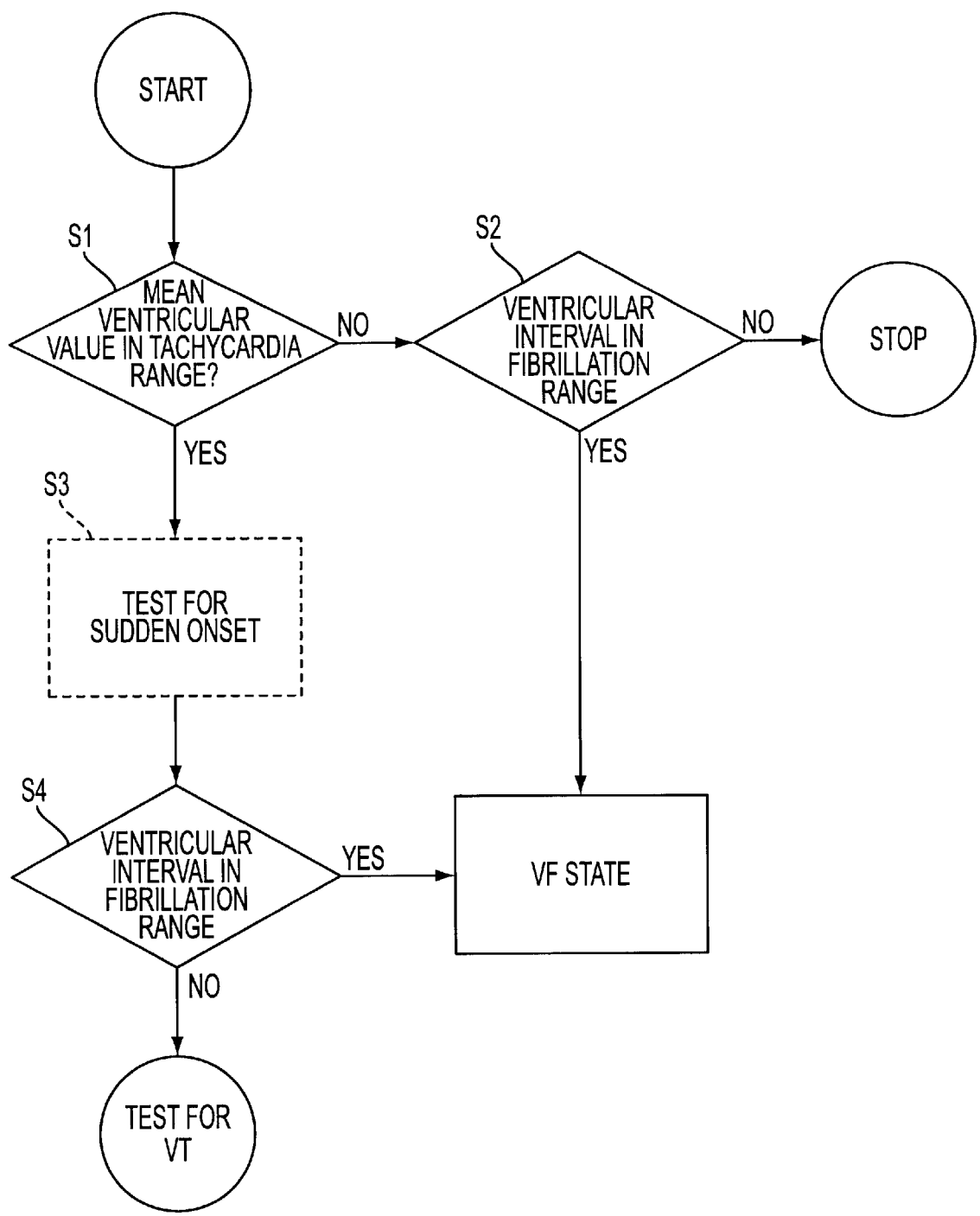
FIGS. 5a and 5b, a flow chart of the process in distinguishing a ventricular tachycardia from a supraventricular tachycardia using a device of FIG. 1.
Figure 5B:
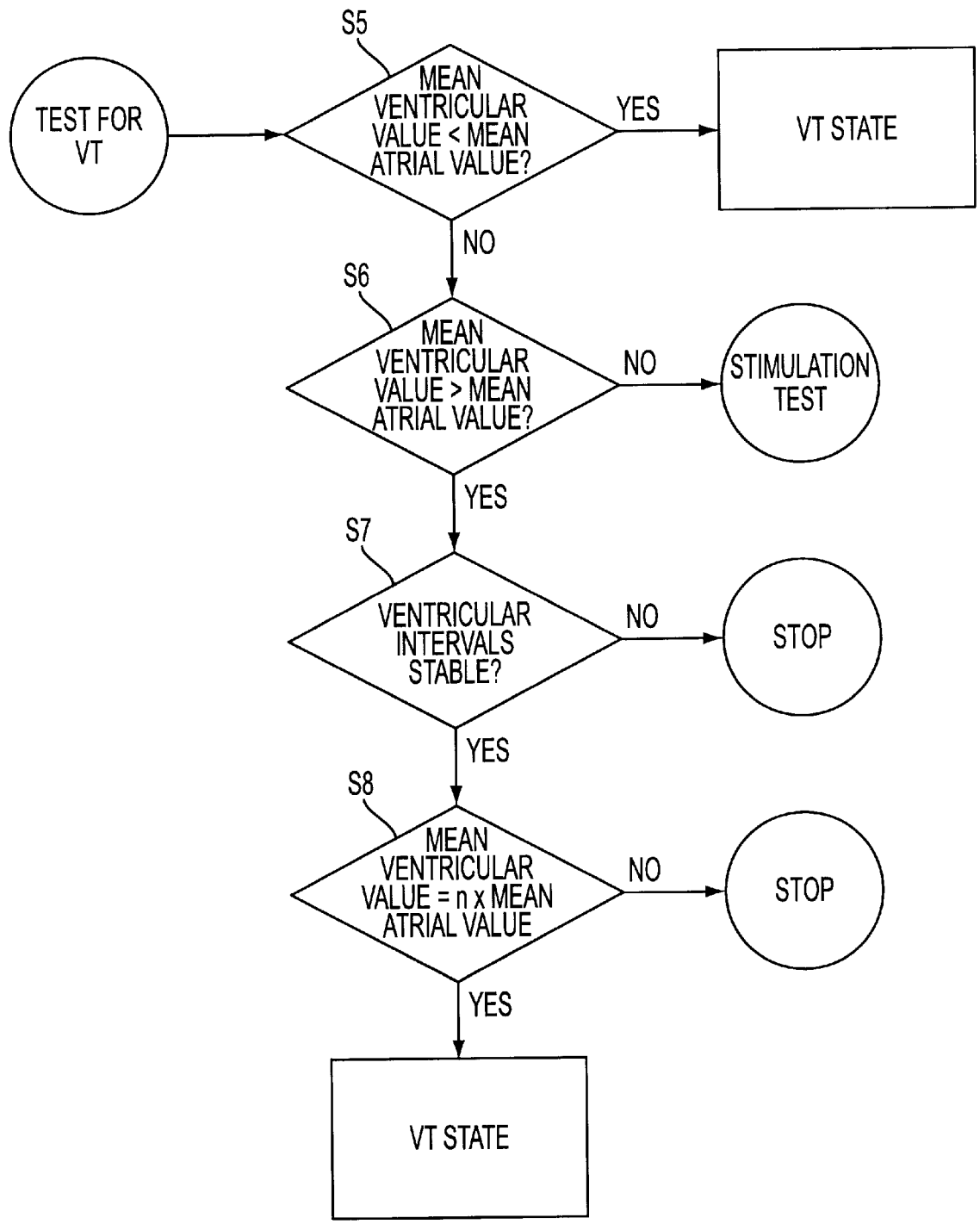

Step S4 in FIG. 5a means that after the question of sudden onset is asked, it is also asked whether the RR interval value is in the aforementioned range (3). If so ("yes" in step S4), then a ventricular fibrillation or "VF state" is involved, which should be treated as mentioned above (where the answer is "no" instep S2). If not ("no" in step S4), then other criteria ("test for VT") for classifying the tachyarrhythmia are checked; see the continuation in FIG. 5b.

In a step S5, in the comparator stage 207, a comparison of the RR intervals (mean values) with the PP intervals (mean values) present at the output of the atrial interval detecting device 203b is carried out. If the RR intervals are shorter than the PP intervals ("yes" in step S5), then a ventricular tachycardia ("VT state") is involved.

If the mean values for the RR interval are not shorter than the mean values for the PP interval ("no" in step S5), then in the flow chart one proceeds to a step S6, in which it is asked whether they are longer than the mean values for the PP interval. (In practice, this step can be performed in the same operation as S5.) If not ("no" in step S6), then the process continues with a "stimulation test". Conversely, if this is the case ("yes" in step S6), one continues to step S7.

In step S7, the question is asked whether the RR intervals are stable over time. To that end, preferably the differences between the current mean values for the RR interval and each of the three preceding mean values for the RR interval are compared with a predetermined stability criterion, instability is assumed to exist if the criterion is met in all three comparisons.) If the RR or ventricular intervals are not stable ("no" in step S7), then the test is discontinued ("stop") with the finding that no ventricular tachycardia is present. Conversely, if they are stable ("yes" in step S7), then one continues to a step S8. The components required for this step are again not shown in FIG. 1.

In step S8, in comparator stage 207, it is asked whether the mean value for the RR interval picked up at the output of the first calculation unit 203a is an integral multiple of the mean value for the PP interval picked up at the output of the second calculation unit 203b. This operation is described above with reference to FIG. 2. If it is found that the mean RR value is an integral multiple of the mean PP value—and in particular is equal to it ("yes" in step S8)—then the test is discontinued ("stop")—again with the result that no ventricular tachycardia is found. What is involved then is an n:1 atrial tachycardia conducted into the ventricle. Conversely, if it is found that it is not an integral multiple ("no" in step S8), then ventricular tachycardia is present.

The test to be performed if the RR and PP intervals of the spontaneous heart actions approximately match in amount, by means of a train of ventricular stimulations ("stimulation test" in FIG. 5b) proceeds basically as follows, in the arrangement of FIGS. 1–4:

In response to the output of a signal CL2 characterizing the PP/RR match by the comparator stage 207, the flip-flop 31 changes the state of its output and thus of the input of the (previously blocked) and gate 37. Upon the next spontaneous ventricular action, moreover, via the blocking member 35 (which still switches through an arriving signal at this moment and blocks as a result of the signal), an output signal R arrives from the ventricular action detecting device 201a, whereupon the AND gate 37 switches open and activates the dividers 33, 36, counters 34, 323 and the evaluation unit 210b.

As a result, counting of the time signals t of the timer 202 by the counter 34 is initiated, which leads to the output of a stimulation control signal STIM by the counter upon reaching the current counting value adjusted via the calculation unit 32. The counter adjustment value, in the first stage of the "stimulation test", is the result of a subtraction of a basic decrement $\Delta_0$, stored in the basic decrementing memory 322, from the last (mean) RR interval, stored in the memory 321, the subtraction being done in the subtraction stage 325, because at this moment the counter 323 is at i=1, so that the basic decrement is not multiplied in the multiplier stage 324. The outputting of the output signal—which is also supplied to the 1:n divider 33—causes a stimulation pulse in the ventricle to be output at an "early" time S1, which is earlier, by the timing amount $\Delta_1$, than the next spontaneous heart action to be expected. Afterward, the counter 34 automatically resets itself and waits for a new activation pulse.

Such a pulse appears upon the detection of an $(m+1)^{th}$ R wave, after m R waves have been rendered inoperative by the blocking member 35, because via the 1:m divider 36, the blocking member is reset after the $m^{th}$ subsequent ventricular action (m is programmable via the input unit 8 and is reset to 8, for example). The counter 34 thereupon begins to run again, and a different counting value is established by the calculation unit 32. This value is obtained, correspondingly to the now-reached counter status i=2 of the counter 323, by subtraction of the basic decrement, multiplied by two in the multiplier stage ($\Delta_2=2\Delta_0$) from the most recent RR interval stored in the memory 321. The stimulus $S_2$ initiated by the output signal of the counter now has a timing that is made earlier by $2\Delta_0$. This procedure is repeated in the context of a test for a programmed number n (such as 5) of different decrements. After that, the 1:n divider 33 outputs an output signal which resets the flip-flop 31 and thus ends the test program.

In every stage of the test—controlled in each case after m intervening spontaneous heart actions by a new output signal of the AND gate 37—the respective $\Delta_i$ value from the multiplier stage 324 is written into the memory 2084 of the evaluation unit 208b and the corresponding atrial interval value $PP_i$ is written into the memory 2082. At the end of the test—initiated by the output signal of the divider 33—the memory contents of 2082 and 2084 are read out, and in stages 2086 through 2088 the rise in the function curve $PP_i=f(RS_i)$ is determined, and it is ascertained whether it is below a threshold value stored in the criteria memory 209b, or in other words whether the atrial intervals PPi remain substantially constant, while RSi rises. If so, then the fact that an SVT is involved is indicated by the output of the signal CL3.

Figure 6:
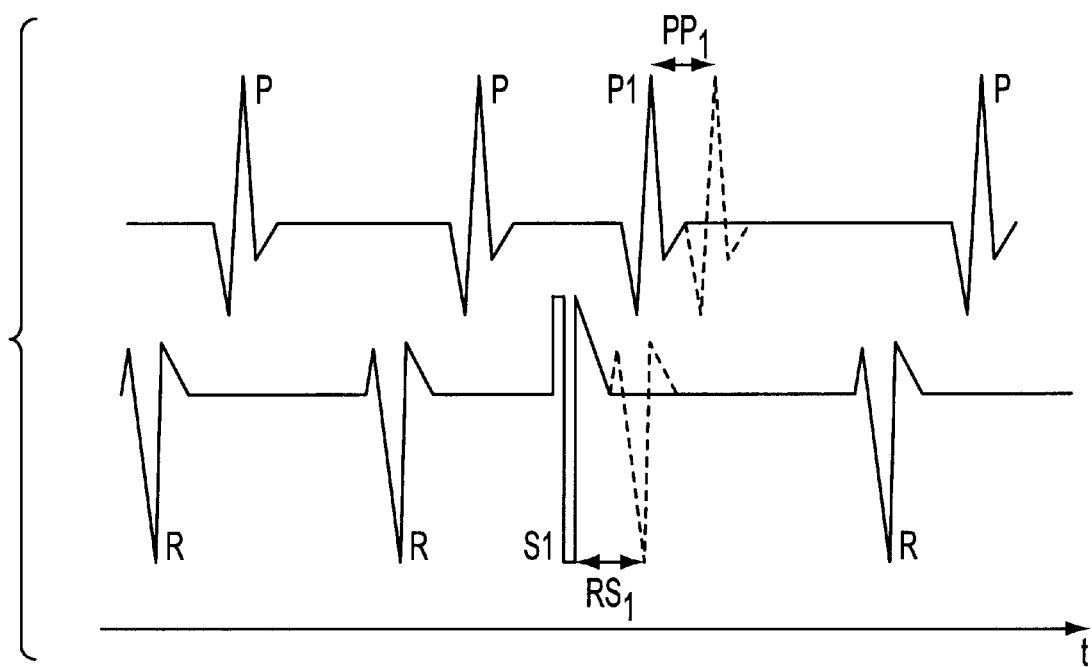
FIG. 6, a graph illustrating the functional principle.

In FIG. 6, the functional principle of the above-described test is illustrated by comparing a plotting of the atrial signals (top) and ventricular signals (bottom) on the same time axis. It can be seen that a ventricular early stimulus that is earlier, by the period $\Delta_1$, than an expected spontaneous ventricular action R (shown in dashed lines) has induced a reaction $P_1$ in the atrium that is earlier, by the amount $PP_1$, than an expected spontaneous atrial action P (shown in dashed lines).

The invention is not limited in its embodiment to the exemplary embodiments discussed above. On the contrary, a number of variants are conceivable that make use of the embodiment shown even in different types of versions. In particular, the block circuit diagrams are not in any way to be understood as limiting. For instance, the test sketched out above may also be performed—given a suitably modified function block circuit diagram—with a sequence of fixedly programmed decrementing values that are not an integral multiple of a basic decrement, for instance with a sequence of 50 msec—80 msec—110 msec—140 msec—170 msec. In the process shown in the flow chart as well, variation can be done by simplifying it or by employing additional test criteria.

What is claimed is:

1. A device for determining tachycardial heart rhythm disturbances, comprising:

a stimulation pulse generator;

a ventricular stimulation electrode;

an electrode line having a first end and a second end wherein, the first end is connected to the output of the stimulation pulse generator and the second end is connected to the stimulation electrode;

one sensor electrode in the atrium of a heart;

one sensor electrode in the ventricle of a heart;

an atrial action detecting device connected on the input side to the atrial sensing electrode;

a ventricular action detecting device connected on the input side to the ventricular sensing electrode;

a timer;

an atrial interval detecting device connected to the timer, for detecting the chronological spacing of successive atrial actions;

a ventricular interval detecting device connected to the timer, for detecting the chronological spacing of successive ventricular actions;

a comparator unit connected on the input side to the outputs of the atrial interval detecting device and the ventricular interval detecting device, wherein the comparator unit compares the chronological spacings of successive atrial actions and successive ventricular actions and outputs a stimulation inducing signal;

an evaluation device connected to the output of the atrial interval detecting device for detecting and evaluating changes, caused by the ventricular stimulation pulse in the atrial intervals and for outputting a tachycardia classification signal that characterizes the outcome of the evaluation; and a stimulation control device having an input connected to an output of the evaluation device, the output of the comparator unit, the timer, the output of the ventricular action detecting device, and the output of the ventricular interval detecting device, and connected on the output side to the stimulation pulse generator, said stimulation control device for controlling the output of a train of stimulation pulses at such intervals as occur between the stimulation pulses of a plurality of spontaneous ventricular actions at a time, with the definition of an interval varying within the train in a predetermined way, of each ventricular stimulation pulse from the preceding or next expected spontaneous ventricular action.

2. The device of claim 1, wherein the stimulation control device further includes a stimulation time calculating unit, said stimulation time calculating unit comprising one of (1) a decrementing memory for storing a predetermined value of the ventricular stimulation time interval and a means for calculating further values from the stored value and (2) a memory for a plurality of predetermined values.

3. The device of claim 1, wherein the evaluation device further comprises a first memory for storing the time intervals of a plurality of predetermined pairs of ventricular stimulation pulses and expected spontaneous ventricular actions, a second memory for storing the time intervals of an equal plurality of corresponding pairs of atrial actions ($PP_i$), and means for setting the memory contents of the first and second memories into relation with one another.

4. The device of claim 3, wherein the means for setting the contents into relation with one another further comprises a correlation stage, a differentiation member connected at least indirectly to the output of the correlation stage, and a comparator unit.

5. The device of claim 4, wherein the comparator unit includes a criteria memory for storing an evaluation criterion for correlating the ventricular stimulus and ventricular action time intervals and the atrial action time intervals, which evaluation criteria are input to the comparator unit of the evaluation device.

6. The device of claim 1, further comprising at least one of means for adjusting a predetermined number of ventricular stimulation pulses of a test sequence and means for adjusting a predetermined number of spontaneous ventricular actions to be allowed between the stimulations of a test sequence.

7. The device of claim 6, further comprising an input unit and wherein the means for adjusting a predetermined number of ventricular stimulation pulses and the means for adjusting a predetermined number of spontaneous ventricular actions are programmable via the input unit.

8. The device of claim 1 utilized as part of an implantable stimulation device.

9. The implantable stimulation device of claim 8 utilized as a combined cardiac pacemaker/cardioverter.

10. The device of claim 1, utilized as part of a cardiac therapy appliance wherein the output of the evaluation device is connected to at least one of a stimulation pulse generator and a defibrillation pulse generator in such a way that the tachycardia classification signal output serves to control an operation of at least one of a cardiac pacemaker and a defibrillator.

* * * * *

UNITED STATES PATENT AND TRADEMARK OFFICE
CERTIFICATE OF CORRECTION

PATENT NO : 6,035,232
DATED : March 7, 2000
INVENTOR(S) : Thong et al.

It is certified that error appears in the above-identified patent and that said Letters Patent is hereby corrected as shown below:

On the title page, change line [73] to read --Biotronik Mess- und Therapiegeraete GmbH & Co. Ingenieurbuero Berlin--

Signed and Sealed this

Ninth Day of January, 2001

Attest:

Q. TODD DICKINSON

*Attesting Officer*   *Commissioner of Patents and Trademarks*